United States Patent

Burstein

[11] Patent Number: 6,121,413
[45] Date of Patent: Sep. 19, 2000

[54] HEAT TREATMENT OF ULTRA HIGH MOLECULAR WEIGHT POLYETHYLENE

[76] Inventor: Albert H. Burstein, 636 Mourning Dove Dr., Sarasaota, Fla. 34236

[21] Appl. No.: 09/302,515

[22] Filed: Apr. 30, 1999

[51] Int. Cl.[7] .................................. B28B 3/20; C08F 6/00
[52] U.S. Cl. ........................ 528/503; 528/176; 264/176.1
[58] Field of Search ................................... 528/503, 176; 264/176.1

[56] References Cited

U.S. PATENT DOCUMENTS

| | | | |
|---|---|---|---|
| 3,944,536 | 3/1976 | Lupton et al. | 428/364 |
| 4,587,163 | 5/1986 | Zachariades | 428/292 |
| 4,888,141 | 12/1989 | Bastiaansen et al. | 264/22 |
| 4,996,011 | 2/1991 | Sano et al. | 264/28 |
| 5,030,402 | 7/1991 | Zachariades | 264/138 |
| 5,037,928 | 8/1991 | Li et al. | 526/352 |
| 5,468,842 | 11/1995 | Howard, Jr. | 528/481 |
| 5,478,906 | 12/1995 | Howard, Jr. | 526/352 |
| 5,621,070 | 4/1997 | Howard, Jr. | 528/481 |
| 5,721,334 | 2/1998 | Burstein et al. | 526/352 |

FOREIGN PATENT DOCUMENTS

WO 97/29895  8/1997  WIPO.

OTHER PUBLICATIONS

ASTM Committee D–20 on Plastics (Designation D: 4020–96): "Standard Specification for Ultra–High Molecular–Weight Polyethylene Molding and Extrusion Materials", *Annual Book of ASTM Standards*, vol. 08.01, pp. 1–5, Pub. Sep. 1996.

ASTM Committee F–4 on Medical and Surgical Materials and Devices (Designation F:648–98): "Standard Specification for Ultra–High–Molecular–Weight Polyethylene Powder and Fabricated Form for Surgical Implants", 1994 *Annual Book of ASTM Standards*, vol. 08.01, pp. 1–6, Pub. Jun. 1998.

*Primary Examiner*—Terressa M. Boykin
*Attorney, Agent, or Firm*—Dreier & Baritz LLP.

[57] ABSTRACT

The present invention provides a method for reducing the modulus of elasticity of a polymeric article, while at the same time maintaining its yield strength, crystallinity and elongation to rupture to be the same as the polymeric article prior to its heating and quenching treatment.

5 Claims, 4 Drawing Sheets

HEAT TREATMENT OF ULTRA HIGH MOLECULAR WEIGHT POLYETHYLENE

FIELD OF THE INVENTION

The present invention relates to a process for treating preformed/prefabricated polymeric articles for use as or including biomedical implants. More specifically, the present invention relates to a process for treating polymeric articles made from ultra high molecular weight polyethylene (UHMWPE) that have been molded into the final or near final configuration, to lower their modulus of elasticity.

BACKGROUND OF THE INVENTION

Ultra high molecular weight polyethylene (UHMWPE) is very resistant to impact and scratches, is known for self-lubrication, has a high melting viscosity, and typically has a weight average molecular weight in excess of 1,000,000, as determined in accordance with ASTM D-4020 viscosity methods. UHMWPE is used for preparing bearing surfaces, such as biomedical implants, e.g., orthopaedic implants, such as tibial plateaus, patellar buttons of prosthetic knee implants, hip implants, etc., typically made by either machining the components from a solid block of UHMWPE or molded directly from native (virgin) UHMWPE powder.

It is known that a major problem with total joint implants prepared by conventional molding and/or machining is wear and surface damage of the article from generated UHMWPE particles (debris) that can function as abrasives to the implant under contact stress. Reduction of contact stress may minimize debris generation, and wear and surface damage.

International Application, WO 97/29895, published on Aug. 21, 1997 (Burstein and Li) teaches that according to Bartel, et al. *Trans of the ASME*, 107, 193–199 (1985) "contact stress is a function of the elastic modulus of the bearing material in a contact bearing joint such as a knee joint," and it is desirable to produce an UHMWPE material with the lowest possible modulus of elasticity, (modulus), which retains the desirable strength properties of conventional UHMWPE. An implant can be prepared by machining or molding by a process other than that described in the above mentioned Burstein and Li patent application.

A successful attempt of producing UHMWPE with a low modulus UHMWPE material of between 500 MPa and 900 MPa is achieved through the controlled mold-quench process of the Burstein and Li International Patent Application discussed above. The Burstein and Li application discloses an invention where UHMIWPE is molded from a powder and at the end of the elevated heat—pressure process step the molded article is subjected to a quenching operation to produce an UHMWPE product with a lowered modulus of elasticity Furthermore, the Burstein and Li process requires careful monitoring of mold body temperatures for the production of fully compacted non-distorted components that do not display surface cavitation. The Burstein and Li process does not relate to the lowering the modulus of elasticity of UHMWPE articles which have been previously prepared and removed from a mold or machining device to a finished dimension because the very surfaces which would typically be quenched to obtain the benefits of reduced modulus (e.g. the articulating surfaces of a total knee joint tibia component) must be carefully cooled in the heat pressing process well before the conclusion of the formation process. A near dimension part is one that allows a small, e.g. 0.025 inches, amount of additional material to allow for a finished machine cut.

Other processes for treating UHMWPE articles, such as U.S. Pat. Nos. 5,621,070 to Howard and U.S. Pat. No. 5,030,402 to Zachariades teach heating UHMWPE articles at temperatures in excess of 200° C. In the Howard patent, rapid cooling is taught to be deleterious to the formation of the desired product.

Thus a need exists to provide biomedical implants having a low modulus of elasticity, between 500 MPa and 900 MPa, from any high modulus preformed or prefabricated polymeric article without resorting to the sophisticated control requirements of the prior art.

SUMMARY OF THE INVENTION

The present invention provides a method for reducing the modulus of elasticity of a polymeric biomedical article, while at the same time maintaining its yield strength to be greater than or equal to about 20 MPa, with an elongation to rupture greater than about 300%, a crystallinity less than about 60% crystallinity, a density less than or equal to about 0.935 g/cc and an average weight average molecular weight of between about 1 million and about 10 million (as determined by conventional viscosity methods such as ASTM D-4020-96 incorporated herein by reference).

According to the present invention, a preformed or prefabricated UHMWPE article, formed by traditional methods, and having a weight or number average molecular weight of between about 1 million and about 10 million is placed in a thermoregulated supportive fixture and heated to a temperature above the melting temperature of the UHMWPE, between about 130° C. to 190° C. Thereafter, the heated article is rapidly cooled. e.g., quenched, to reduce its temperature below the melting temperature of the UHMWPE.

An object of the invention is to provide a process for reducing the modulus of elasticity of a polymeric article without degrading its other physical properties below useful levels.

It is a further object of the present invention to treat a previously formed UHMWPE article to reduce its modulus of elasticity, while at the same time maintaining its yield strength and elongation to rupture at useful levels.

An object of this invention is to provide a process that uses relatively simple, standard equipment and provides quenching rates that are maximized since the cooling fluid is in direct contact with the component surfaces.

These and other objects and advantages will become more apparent when considered in light of the following detailed description, drawings and appended claims.

DETAILED DESCRIPTION OF THE INVENTION

Figure 1:
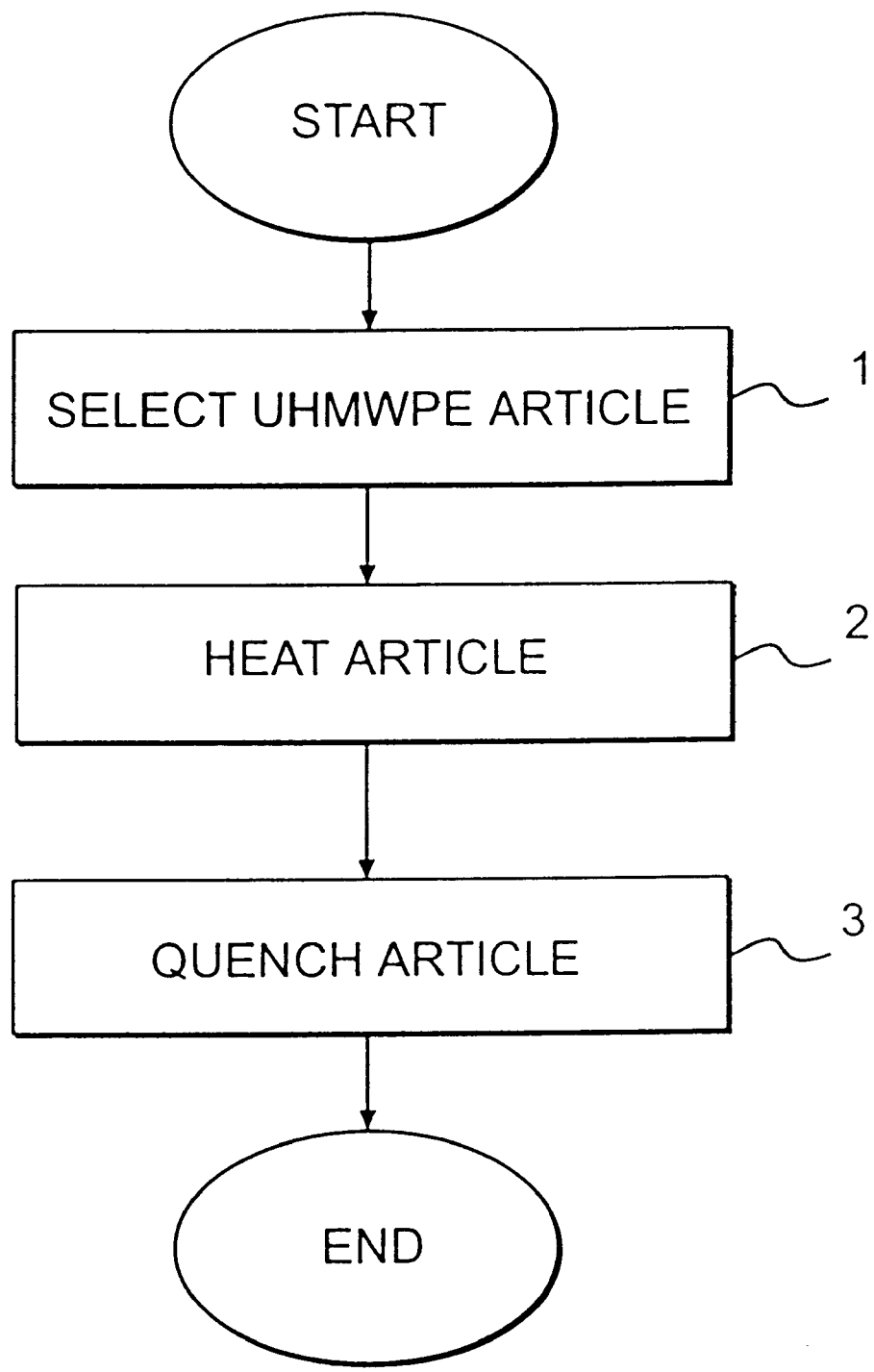
FIG. 1 is a flow diagram of the process according to the present invention.

The process of the present invention may be conducted at any pressure that is used in a conventional annealing process, for example ambient pressure. The process may be conducted in any atmosphere that is not detrimental to UHMWPE when raised above its melting point, preferably air or nitrogen. As shown in FIG. 1, a premolded or prefabricated article 1 is placed or located in a supportive device, e.g. tray or fixture 2, that can heated by any well known technique. The supportive device prevents warpage of the article. Once article 1 is located in the tray or fixture 2, the article 1 and support tray or fixture are then heated in an ambient atmosphere to above the melting temperature of UHMWPE 130° C. to about 140° C. In one embodiment of the invention, the article and tray or supportive fixture 2 are heated to a temperature between 132° C. and 152° C. for parts having complex shapes and closely toleranced surfaces and between 132° C. and 172° C. for parts having simpler shapes and less critical tolerances. The actual temperature that is selected for any particular size, shape and dimensional tolerance of the component will be the highest temperature that does not produce dimensional changes outside the tolerance limits e.g., surface tolerance of ±0.010 inches and produces the degree of elastic modulus decrease desired, an elastic modulus between 500 MPa and 900 MPa. After article 1 has been heated to above its melting point, it is quickly removed from the oven and subjected to a quench fluid. If convenient, the article may be left on the tray or support fixture, if the article will be surrounded by the quench fluid. The quench fluid may be contained in an immersion bath with or without agitation, a spray chamber, or any similar device which can lower the surface temperature of the UHMWPE component without chemical reaction to alter the material. Suitable fluids include water, although other highly conductive inert fluids which may be cooled to near or below the freezing point of water may be used. When the component has cooled to below the melting temperature of UHMWPE throughout its thickness, it is removed from the quenching chamber.

EXAMPLES

Figure 2:
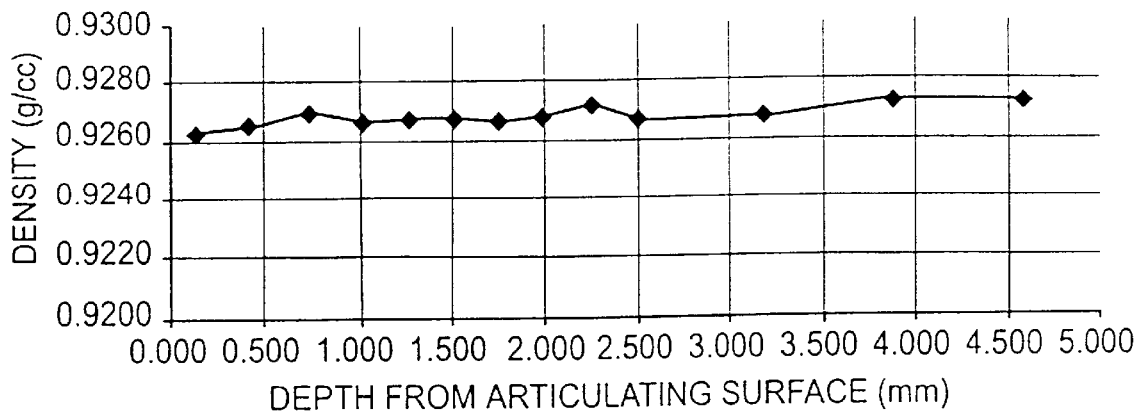
FIG. 2 is a graph depicting the density profile for Example 1 as a result of conventional processing.
Figure 4:
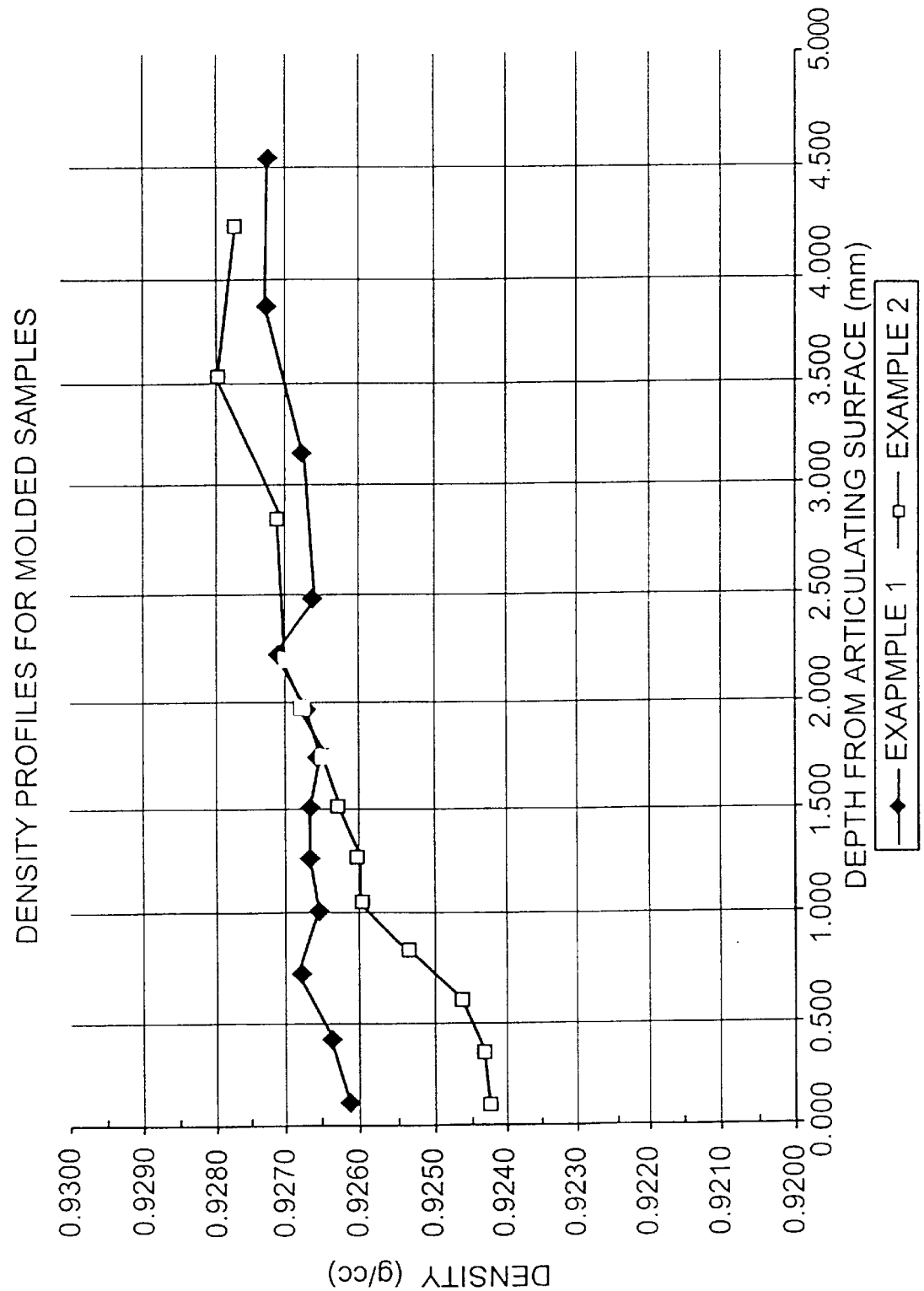
FIG. 4 is a graph comparing the density profiles of Example 1 and Example 2.

Ultra high molecular weight polyethylene, GUR 1050, having a weight average molecular weight corresponding to an intrinsic viscosity of 29 dl/g and a reduced specific viscosity of 35 dl/g and available from Ticona was molded into two tibial tray insert bearing components designated Example 1 and Example 2 by conventional molding techniques, such as those disclosed in WO 97/29895. Example 1, the molded control sample, was not subjected to any heat treatment. Samples for density measurements were obtained from Example 1 by obtaining sample slices from a central transverse core of Example 1. Density data for control Example 1 is obtained by using a standard density column, as taught in ASTM D 1505-96, Standard Test for Density of Plastics by the Density Gradient Technique. The density gradient technique employs a water-alcohol mixture of varying concentration to float specimens in a known, calibrated column and is shown below in TABLES 1–2, and depicted in FIGS. 2 and 4.

TABLE 1

| EXAMPLE 1 | | | |
|---|---|---|---|
| Column Reading 1 | Density (g/cc) | Column Reading 2 | Density (g/cc) |
| 44.1 | 0.9200 | 44.1 | 0.9200 |
| 34.8 | 0.9260 | 39.8 | 0.9230 |
| 30.9 | 0.9280 | 34.8 | 0.9260 |
| 39.6 | 0.9230 | 30.9 | 0.9280 |

TABLE 2

| Slice | Depth (mm) | Column 1 position | Density (g/cc) | Column 2 Position | Density (g/cc) | Difference | Depth (mm) | Density (g/cc) |
|---|---|---|---|---|---|---|---|---|
| 1 | 0.137 | 34.9 | 0.9259 | 33.9 | 0.9265 | −0.0005 | 0.137 | 0.9262 |
| 2 | 0.430 | 34.1 | 0.9264 | 33.7 | 0.9266 | −0.0002 | 0.430 | 0.9265 |
| 3 | 0.737 | 33.2 | 0.9268 | 33.0 | 0.9269 | −0.0001 | 0.737 | 0.9269 |
| 4 | 1.019 | 33.7 | 0.9266 | 33.5 | 0.9267 | −0.0001 | 1.019 | 0.9266 |
| 5 | 1.270 | 33.4 | 0.9267 | Stuck | | | 1.270 | 0.9267 |
| 6 | 1.503 | 33.3 | 0.9268 | 33.5 | 0.9267 | 0.0001 | 1.503 | 0.9267 |
| 7 | 1.735 | 33.7 | 0.9266 | 33.5 | 0.9267 | −0.0001 | 1.735 | 0.9266 |
| 8 | 1.967 | 33.4 | 0.9267 | 33.3 | 0.9268 | −0.0001 | 1.967 | 0.9267 |
| 9 | 2.228 | 32.6 | 0.9271 | 32.5 | 0.9272 | −0.0001 | 2.228 | 0.9272 |
| 10 | 2.485 | 33.6 | 0.9266 | 33.5 | 0.9267 | −0.0001 | 2.485 | 0.9266 |
| 11 | 2.712 | 0.0 | 0.9458 | 0.0 | 0.9438 | | | |
| 12 | 2.947 | 0.0 | 0.9458 | 0.0 | 0.9438 | | | |
| 13 | 3.179 | 33.4 | 0.9267 | 33.1 | 0.9269 | −0.0002 | 3.179 | 0.9268 |
| 14 | 3.408 | 0.0 | 0.9458 | 0.0 | 0.9438 | | | |
| 15 | 3.641 | 0.0 | 0.9458 | 0.0 | 0.9438 | | | |
| 16 | 3.871 | 32.5 | 0.9272 | 32.1 | 0.9274 | −0.0002 | 3.871 | 0.9273 |
| 17 | 4.102 | 0.0 | 0.9458 | 0.0 | 0.9438 | | | |
| 18 | 4.337 | 0.0 | 0.9458 | 0.0 | 0.9438 | | | |
| 19 | 4.569 | 32.5 | 0.9272 | 32.3 | 0.9273 | −0.0001 | 4569 | 0.9272 |

The average density throughout the control core (Example 1) is 0.9286 g/cc whereas the maximum density throughout the control core is 0.9273 g/cc.

Figure 3:
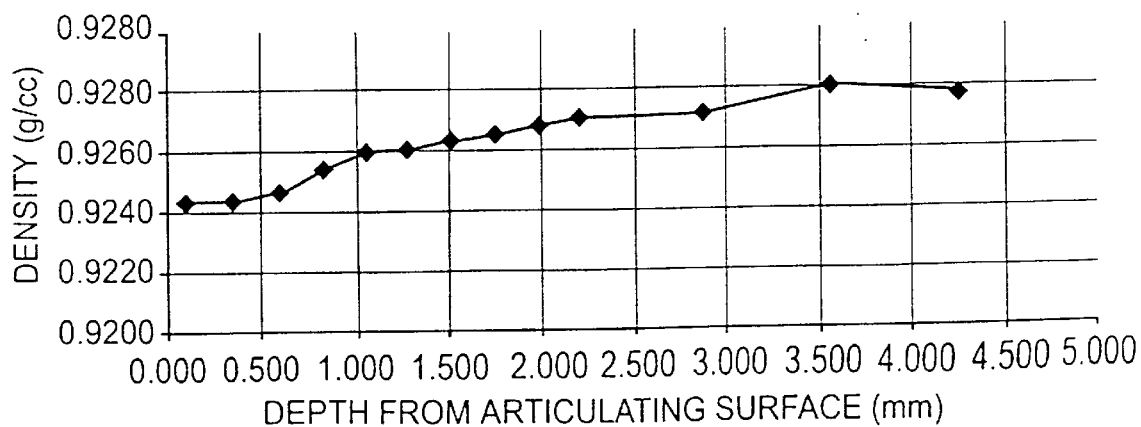
FIG. 3 is a graph depicting the density profile for Example 2 processed in accordance with the present invention.

Example 2, the molded tibial tray insert component, formed from GUR 1050 was heated to about 145° C., which is above the melting point of UHMWPE, until it was fully melted, verified by its translucent state, for approximately ten minutes and then quenched in an ice/water bath. Samples for density measurements were obtained from Example 2 by taking slices from the central transverse core. Example 2 density data for the treated component and slices were obtained using a standard density column, as taught in the ASTM standard D1505-96, and shown below in TABLES 3 and 4, and depicted in FIGS. 3 and 4.

TABLE 3

EXAMPLE 2

| TABLE 1 | | TABLE 2 | |
|---|---|---|---|
| Column Reading 1 | Density (g/cc) | Column Reading 2 | Density (g/cc) |
| 44.1 | 0.9200 | 44.2 | 0.9200 |
| 39.8 | 0.9230 | 39.8 | 0.9230 |
| 34.8 | 0.9260 | 34.9 | 0.9260 |
| 30.4 | 0.9280 | 31.0 | 0.9280 |

TABLE 4

| | | | | Averages: | | | |
|---|---|---|---|---|---|---|---|
| Slice | Depth (mm) | Column 1 position | Density (g/cc) | Column 2 Position | Density (g/cc) | Difference | Depth (mm) | Density (g/cc) |
| 1 | 0.114 | 37.6 | 0.9243 | | 0.9232 | 0.0011 | 0.114 | 0.9243 |
| 2 | 0.352 | 37.6 | 0.9243 | 37.5 | 0.9244 | −0.0001 | 0.352 | 0.9244 |
| 3 | 0.596 | 37.0 | 0.9247 | 37.1 | 0.9247 | 0.0000 | 0.596 | 0.9247 |
| 4 | 0.829 | | 0.9256 | 35.9 | 0.9254 | 0.0002 | 0.829 | 0.9254 |
| 5 | 1.053 | | 0.9256 | 34.9 | 0.9260 | −0.0004 | 1.053 | 0.9260 |
| 6 | 1.275 | 34.8 | 0.9260 | 34.6 | 0.9262 | −0.0002 | 1.275 | 0.9261 |
| 7 | 1.510 | | 0.9259 | 34.3 | 0.9263 | −0.0004 | 1.510 | 0.9263 |
| 8 | 1.746 | 33.8 | 0.9265 | 33.8 | 0.9266 | −0.0001 | 1.746 | 0.9265 |
| 9 | 1.971 | 33.3 | 0.9267 | 33.1 | 0.9269 | −0.0002 | 1.971 | 0.9268 |
| 10 | 2.197 | | | 32.9 | 0.9270 | −0.0004 | 2.197 | 0.9270 |
| 11 | 2.420 | 0.0 | | 0.0 | 0.9439 | | | |
| 12 | 2.642 | 0.0 | | 0.0 | 0.9439 | | | |
| 13 | 2.873 | 32.6 | 0.9267 | 32.4 | 0.9273 | −0.0003 | 2.873 | 0.9271 |
| 14 | 3.105 | 0.0 | 0.9418 | 0.0 | 0.9439 | | | |
| 15 | 3.369 | 0.0 | 0.9418 | 0.0 | 0.9439 | | | |
| 16 | 3.557 | 30.6 | 0.9279 | 31.0 | 0.9280 | −0.0001 | 3.557 | 0.9280 |
| 17 | 3.789 | 0.0 | 0.9418 | 0.0 | 0.9439 | | | |
| 18 | 4.017 | 0.0 | 0.9418 | 0.0 | 0.9439 | | | |
| 19 | 4.251 | 31.4 | 0.9275 | 31.2 | 0.9279 | −0.0004 | 4.251 | 0.9277 |

Figure 5:
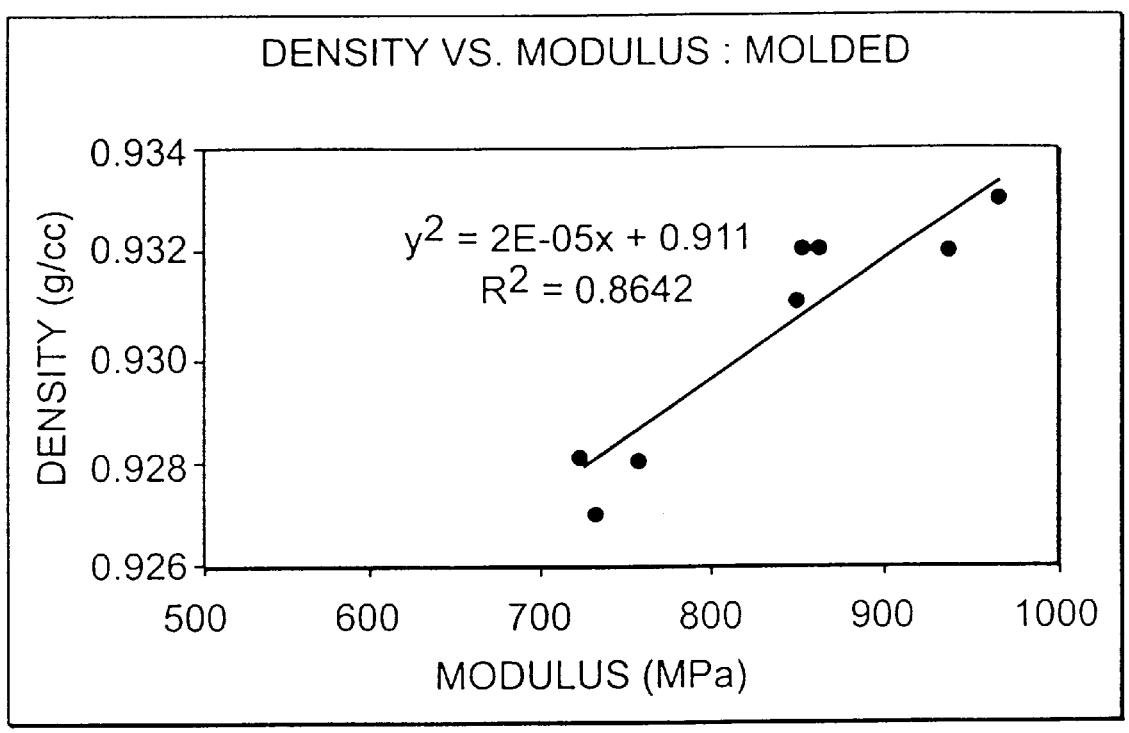
FIG. 5 is a graph of the density versus modulus for the molded sample treated in accordance with the present invention.

The heat treating process according to the present invention demonstrates the production of a low surface density, which corresponds to a low surface modulus as seen from FIG. 5.

EXAMPLE 3

A standard extruded bar of UHMWPE, GUR 4150, molecular weight of approximately $6 \times 10^6$ g/mole was machined into 6 slices that are approximately 0.130 inches thick. Three slices were used as a control, that is, they received no further treatment. The remaining three slices were heated at 145° C., above the melting point of UHMWPE, and quenched in an ice/water bath. Two specimens from each slice were machined for tension testing in accordance with ASTM test F-648-98. The modulus of each specimen was then measured, and the resulting data shown below in TABLE 5. Specimens 6-1 through 6-6 were obtained from the heat treated and quenched samples in accordance with the present invention. Samples 6-7 through 6-12 were obtained from the control.

TABLE 5

TENSILE TEST RESULTS (Modulus)

| SPECIMEN | MODULUS E (MPa) | $R^2$ | AVE. MODULUS E (MPa) | STD. DEV MODULUS, E (MPa) |
|---|---|---|---|---|
| 6-1 | 690 | 0.970 | 689 | 35 |
| 6-2 | 680 | 0.927 | | |
| 6-3 | 751 | 0.914 | | |
| 6-4 | 654 | 0.944 | | |
| 6-5 | 657 | 0.940 | | |
| 6-6 | 701 | 0.931 | | |

TABLE 5-continued

TENSILE TEST RESULTS (Modulus)

| SPECIMEN | MODULUS E (MPa) | $R^2$ | AVE. MODULUS E (MPa) | STD. DEV MODULUS, E (MPa) |
|---|---|---|---|---|
| 6-7 | Data File Bad | | 949 | 34 |
| 6-8 | 959 | 0.930 | | |
| 6-9 | 909 | 0.926 | | |
| 6-10 | 967 | 0.942 | | |
| 6-11 | 921 | 0.945 | | |
| 6-12 | 991 | 0.938 | | |

As shown in the data Table 5, a UHMWPE sample was treated in accordance with the present invention, specimens 6-1 to 6-6, had a directly measured modulus of less than 800 Mpa. In contrast the untreated specimens 6-7 to 6-12 had a modulus of elasticity greater than 900 Mpa.

Table 6 compares the elongation to break, yield strength and ultimate tensile strength in the same samples evaluated in Table 5.

TABLE 6

Tensile Test Results

| | Elongation to Break | | | Yield Strength | | | Ultimate Tensile Strength | | |
|---|---|---|---|---|---|---|---|---|---|
| Specimen | Elongation (%) | Avg. (%) | St. Dev. (%) | Yield (Mpa) | Avg. (Mpa) | St. Dev. (Mpa) | UTS (Mpa) | Avg. (Mpa) | St. Dev. (Mpa) |
| 61-a | 341 | 358 | 21 | 19.9 | 20 | 0.7 | 25.9 | 27 | 2.9 |
| 6-2a | 352 | | | 21.1 | | | 27.9 | | |
| 6-3a | 363 | | | 19.6 | | | 28.4 | | |
| 6-4a | 396 | | | 20.4 | | | 31.0 | | |
| 6-5a | 352 | | | 19.1 | | | 24.7 | | |
| 6-6a | 341 | | | 19.6 | | | 22.9 | | |
| 6-7a | 330 | 348 | 18 | 22.5 | 23 | 1.4 | 39.3 | 40 | 2.6 |
| 6-8a | 352 | | | 21.9 | | | 38.2 | | |
| 6-9a | 341 | | | 21.3 | | | 37.1 | | |
| 6-10a | 330 | | | 23.7 | | | 38.5 | | |
| 6-11a | 374 | | | 23.4 | | | 42.4 | | |
| 6-12a | 363 | | | 25.2 | | | 43.6 | | |

Uts - 27 Mpa  }  The minimum specifications required by the FDA
Yield - 19 Mpa  }  "Data Requirements for Ultrahigh Molecular Weight
% elongation 300%  }  Polyethylene (UHMWPE) Used in Bearings Surfaces for Orthopaedic Devices"

It can be concluded that the Elongation to Break remains above the minimum required value of 300%; the Yield Strength remains above the minimum required value of the 19 MPa; and the Ultimate Tensile Strength meets the minimum required value of 27 MPa. Thus the claimed heat treatment lowers the elastic modulus from approximately 950 MPa to approximately 690 MPa while maintaining the other physical properties at or above the minimum requirements specified in ASTIM-F-648 standard specifications for Ultra-High-Molecular Weight Polyethylene Powder and fabricated form for surgical implants.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. A process for reducing the modulus of elasticity of a prefabricated ultra high molecular weight polyethylene shaped article comprising the steps of:

(a) supporting the prefabricated shaped article, having a first modulus of elasticity, in a device to minimize warpage of the article;

(b) heating the article to a temperature above the melting point of the polyethylene that results in a decrease in the modulus of elasticity of the article while below a temperature that produces substantial dimensional changes outside the desired tolerance limits;

(c) quenching the shaped article with a fluid to a temperature at least below the melting point of the polyethylene; and (d) removing the shaped article from the supporting device, wherein the final product has an ending modulus of elasticity that is below the first modulus of elasticity.

2. An ultra high molecular weight polyethylene biomedical article having a molecular weight of between about 1 million and about 10 million, a yield strength greater than or equal about 20 MPa, an elongation to rupture greater than about 300%, a crystalinity less than about 60% crystalinity, a density less than or equal to about 0.935 g/cc, formed by the process comprising the steps of:

(a) supporting the prefabricated biomedical article, having a first modulus of elasticity, in a device to minimize warpage of the article;

(b) heating the article to a temperature between about 132° C. and about 190° C.;

(c) quenching the article with a fluid to a temperature at least below the melting point of the polyethylene; and (d) removing the article from the supporting device, wherein the final product has an ending modulus of elasticity that is below the first modulus of elasticity.

3. The process accordingly to claim 1, wherein said heating of step (b) includes heating the article to a temperature above its melting point but less than 190° C.

4. The process according to claim 1, wherein said heating includes heating the article to a temperature of between 152° C. and 172° C.

5. The process according to claim 1, wherein said heating includes heating the article to a temperature of between approximately 132° C. and 172° C.

* * * * *